| United States Patent [19] | [11] Patent Number: 4,844,907 |
| --- | --- |
| Elger et al. | [45] Date of Patent: Jul. 4, 1989 |

[54] PHARMACEUTICAL COMPOSITION COMPRISING ANALGESIC AND ANTI-INFLAMMATORY AGENT

[75] Inventors: Gordon A. Elger, Huntingdon; Stewart T. Leslie; Sandra T. A. Malkowska, both of Cambridge, all of United Kingdom; Ronald B. Miller, Basel, Switzerland; Philip J. Neale, Cambridge, United Kingdom

[73] Assignee: Euroceltique, S.A., Luxembourg, Luxembourg

[21] Appl. No.: 896,214

[22] Filed: Aug. 14, 1986

[30] Foreign Application Priority Data

Aug. 28, 1985 [GB] United Kingdom ............... 8521350

[51] Int. Cl.⁴ .......................... A61K 9/20; A61K 9/24; A61K 9/50
[52] U.S. Cl. ..................................... 424/465; 424/470; 424/472; 424/475; 424/477; 424/479; 424/480; 424/481; 424/482; 424/499; 424/500; 424/501; 424/502
[58] Field of Search ............... 424/465, 470, 480, 472, 424/475, 477, 479, 481, 482, 499, 500, 501, 502

[56] References Cited

U.S. PATENT DOCUMENTS

| 2,738,303 | 3/1956 | Blythe .................................. 424/458 |
| 3,558,768 | 1/1971 | Klippel ................................ 424/480 |
| 3,950,508 | 4/1976 | Mony et al. .................... 424/480 X |
| 4,601,894 | 7/1986 | Hanna et al. ....................... 424/480 |
| 4,606,909 | 8/1986 | Bechgaard et al. ............ 424/480 X |

*Primary Examiner*—Thurman K. Page
*Attorney, Agent, or Firm*—Steinberg & Raskin

[57] ABSTRACT

A pharmaceutical composition in the form of a multiphase (especially a bilayered, optionally coated) tablet. The tablet has a narcotic analgesic phase containing a therapeutically effective quantity of a narcotic analgesic or an analgesically effective salt thereof (e.g. codeine phosphate) and a non-steroidal anti-inflammatory phase containing a therapeutically effective quantity of a non-steroidal anti-inflammatory carboxylic acid or an anti-inflammatory salt or ester thereof (e.g. ibuprofen). The narcotic analgesic phase is free from a non-steroidal anti-inflammatory carboxylic acid or salt or ester thereof, stearic acid and stearate salt, and the non-steroidal anti-inflammatory phase is free from a narcotic analgesic or salt thereof, stearic acid and a stearate salt. Further, both the narcotic analgesic phase and the non-steroidal anti-inflammatory phase contain a self-lubricating, compression aid, especially a self-lubricating, direct compression aid, such as microcrystalline cellulose.

13 Claims, No Drawings

PHARMACEUTICAL COMPOSITION COMPRISING ANALGESIC AND ANTI-INFLAMMATORY AGENT

This invention relates to a pharmaceutical composition, in particular to a pharmaceutical composition for the relief of mild to severe pain and for the treatment of inflammation in musculo-skeletal disorders.

Narcotic analgesics, such as codeine and dihydrocodeine, have been used in the relief of pain, especially mild to severe pain. Severe pain, in particular, requires the use of large and increasing doses of a narcotic analgesic.

A major disadvantage of narcotic analgesics is that patients may develop a dependence and tolerance to their action. Further adverse reactions, such as respiratory and circulatory depression, are observed when large doses of narcotic analgesics are used.

Non-steroidal anti-inflammatory drugs, such as ibuprofen, have been used in rheumatic and degenerative diseases of the joints, for reducing platelet adhesiveness and for dental pain.

European Patent Application No. 68838A (Upjohn) describes the synergistic effect obtained for the management of moderate to severe pain when a combination of narcotic analgesic and ibuprofen is administered.

In the Examples of EP No. 68838A, tablets containing morphine, ibuprofen and magnesium stearate as lubricant, are disclosed. The applicant also states, at page 9, lines 22 to 26, that tablets containing ibuprofen and codeine may be prepared simply by replacing the morphine in the exemplified tablets with codeine.

The present inventors have found that tablets containing a narcotic analgesic, such as codeine, a non-steroidal anti-inflammatory carboxylic acid, such as ibuprofen, and magnesium stearate, as described in EP No. 68838A, exhibit serious incompatability, poor crushing strength and long disintegration times.

It is therefore a primary object of the present invention to provide a tablet containing both a narcotic analgesic and a non-steroidal anti-inflammatory carboxylic acid which overcomes, to a substantial degree, the above problems.

Other objects and advantages of the present invention will become apparent from the following detailed description thereof.

According to the present invention there is provided a pharmaceutical composition in the form of a multiphase tablet comprising at least one narcotic analgesic phase containing a therapeutically effective quantity of a narcotic analgesic or an analgesically effective salt thereof and at least one non-steroidal anti-inflammatory phase containing a therapeutically effective quantity of a non-steroidal anti-inflammatory carboxylic acid or an anti-inflammatory salt or ester thereof wherein the at least one narcotic analgesic phase is free from a non-steroidal anti-inflammatory carboxylic acid or salt or ester thereof, stearic acid and a stearate salt, and the at least one non-steroidal anti-inflammatory phase is free from a narcotic analgesic or salt thereof, stearic acid and a stearate salt, and further wherein, both the at least one narcotic analgesic phase and the at least one non-steroidal anti-inflammatory phase contain at least one self-lubricating, compression aid.

Preferably the self-lubricating compression aid is a self-lubricating, direct compression aid.

Preferably the composition is in the form of a layered tablet, especially a bilayer tablet. Optionally the layered tablet may be film coated.

The narcotic analgesic may be naturally occurring, semi-synthetic or synthetic. Examples include pentazocine (HCl salt), pethidine (HCL salt) and phenazocine (HBr salt). Preferably, however, the narcotic analgesic is a morphinan-6-ol or a morphinan-6-one derivative, especially morphine (sulphate), ethylmorphine (HCl salt), hdyromorphone (HCl salt), hydrocodone (tartrate), dihydrocodeine (tartrate) and, which is particularly preferred, codeine (phosphate).

Analgesically effective salts of the narcotic analgesics of the present invention must be pharmaceutically acceptable.

The non-steroidal anti-inflammatory carboxylic acid will generally be an aromatic or heterocyclic carboxylic acid. Examples include aspirin, fenbufen, flufenamic acid, indomethacin, meclofenamic acid (sodium salt), sulindac and tolmetin (sodium salt). Preferably, however, the non-steroidal anti-inflammatory carboxylic acid is a benzeneacetic acid, such as alclofenac, diclofenac (sodium salt) and fenclofenac, a 2-naphthylopropionic acid, such as naproxen (sodium salt), or, which is particularly preferred, a 2-phenylpropionic acid, such as fenoprofen (sodium or calcium salt), flurbiprofen, indoprofen, ketoprofen and, especially, ibuprofen.

Anti-inflammatory effective salts or esters of the non-steroidal anti-inflammatory carboxylic acids of the present invention must be pharmaceutically acceptable, e.g. alkali metal salt and $C_1-C_6$ alkyl esters.

Therapeutically effective quantities of the present narcotic analgesics or salts thereof and non-steroidal anti-inflammatory carboxylic acids or salts or esters thereof will be sufficient, in combination, either to relieve mild to severe pain or to treat inflammatory conditions.

Preferred therapeutically effective quantities of the preferred narcotic analgesics and the preferred non-steroidal anti-inflammatory carboxylic acids of this invention are listed in the Table.

TABLE

| | Therapeutically effective quantity | |
|---|---|---|
| | Preferred Single Dose | Particularly Preferred Single Dose |
| Narcotic Analgesic | | |
| Codeine | 5–60 mg | 7.5–30 mg |
| Dihydrocodeine | 10–60 mg | 20–40 mg |
| Ethylmorphine | 5–60 mg | |
| Hydrocodone | 5–20 mg | |
| Hydromorphone | 1–5 mg | |
| Morphine | 2–120 mg | 5–100 mg. |
| Pentazocine | 10–100 mg | |
| Pethidine | 20–150 mg | |
| Phenazocine | 2.5–20 mg | |
| Non Steroidal Anti-inflammatory Carboxylic Acid | | |
| Aspirin | 200–1000 mg | 300–900 mg |
| Alclofenac | 400–1000 mg | |
| Diclofenac | 25–75 mg | 25–50 mg |
| Fenbufen | 200–900 mg | 300–600 mg |
| Fenclofenac | 200–600 mg | |
| Fenoprofen | 200–800 mg | 300–600 mg |
| Flufenamic acid | 50–250 mg | |
| Flurbiprofen | 25–100 mg | |
| Ibuprofen | 50–800 mg | 200–600 mg |
| Indomethacin | 20–100 mg | 25–75 mg |
| Indoprofen | 50–200 mg | 100–200 mg |
| Ketoprofen | 50–200 mg | |

TABLE-continued

| | Therapeutically effective quantity | |
| --- | --- | --- |
| | Preferred Single Dose | Particularly Preferred Single Dose |
| Meclofenamic acid | 50–200 mg | |
| Naproxen | 250–1000 mg | 500–750 mg |
| Sulindac | 100–200 mg | |
| Tolmetin | 200–800 mg | 200–600 mg |

In a particularly preferred embodiment of the present composition the narcotic analgesic phase contains codeine (as its phosphate salt) and the non-steroidal anti-inflammatory phase contains ibuprofen (as the free acid).

As mentioned above, when the present inventors attempted to prepare narcotic analgesic/non-steroidal anti-inflammatory carboxylic acid (especially codeine/ibuprofen) tablets as in EP No. 68838A they found that the tablets exhibited poor pharmaceutical qualities. This was surprisingly found to be caused primarily by incompatability between the narcotic analgesic (codeine), the non-steroidal anti-inflammatory carboxylic acid (ibuprofen) and the lubricant employed, magnesium stearate.

Having made this observation, the present inventors then overcame these problems by an inventive combination of devices. These were (i) Separating the narcotic analgesic or salt thereof and the non-steroidal anti-inflammatory carboxylic acid or salt or ester thereof in a multi-phase, preferably layered, tablet, (ii) Removing stearic acid and/or stearate salts (especially magnesium stearate) from the composition, and (iii) Adding at least one self lubricating, direct compression aid, preferably a self lubricating, direct compression aid, to the mixtures used to form both the at least one narcotic analgesic and the at least one non-steroidal anti-inflammatory phases of the tablet in order to provide the lubrication necessary in tablet formation.

The self lubricating compression aids, preferably self lubricating, direct compression aids, employed in the present pharmaceutical composition combine at least two properties required of tablet vehicles. First they produce hard, stable tablets via compression, preferably via direct compression, and second they act as a lubricant to facilitate tablet ejection after compression. Examples of such compression aids will be well known to those skilled in the tablet formulation art. Amongst the aids that are preferred in the present composition are Elcema G-250 (Trade Mark, Degussa, cellulose granules derived from powdered cellulose N.F.), Starch 1500 (Trade Mark, Colorcon, a free flowing, directly compressible starch), and, which is particularly preferred, microcrystalline cellulose, especially Avicel (Trade Mark, FMC).

In addition to self lubricating, compression aids, the present composition may also contain, in one or more of its phases, other additives and components, provided they are compatible with the narcotic analgesic or salt thereof and the non-steroidal anti-inflammatory carboxylic acid or salt or ester thereof. Suitable materials include (a) Binders, such as cellulose and its derivatives, e.g. ethyl cellulose hydroxypropylmethyl cellulose, hydroxyethyl cellulose, starches, polyvinyl pyrrolidone, natural gums and gelatin, (b) Glidants, such as talc and fumed silica, (c) Anti-Adherents, such as talc, fumed silica and corn starch, (d) Disintegrants, such as starch and its derivatives, (e.g. sodium starch glycollate), microcrystalline celllose, croscamellose sodium (Ac-Di-Sol, Trade Mark), low substituted hydroxypropyl cellulose and cross-linked polyvinylpyrrolidone, (e) Colorants, Flavorants and Sweeteners.

In addition to the above materials, in a further aspect of the present composition, the at least one non-steroidal anti-inflammatory and/or narcotic analgesic phases may also contain substances suitable for the formation of a controlled release formulation. In particular the phase or phases may contain a hydrated water soluble hydroxy alkyl cellulose, especially hydroxyethyl cellulose, and a higher aliphatic alcohol, especially cetostearyl alcohol, as described in British Pat. No. 1405088 (equivalent to U.S. Pat. No. 3,965,256 and U.S. Pat. No. 4,235,870), the contents of which documents are herein incorporated by way of reference.

Advantageously, the present multi-phase tablet may have, as one of its phases, a protective coating which may, for example, serve to mask the taste of both the non-steroidal anti-inflammatory carboxylic acid or salt or ester thereof and the narcotic analgesic or salt thereof. Suitable coating materials, which must be compatible with both the anti-inflammatory carboxylic acid or salt or ester thereof and the narcotic analgesic or salt thereof will be known to those skilled in this art. An example favoured by the present inventors uses hydroxypropyl methyl cellulose as the film former and propylene glycol as the plasticiser.

The precise amount of non-steroidal anti-inflammatory carboxylic acid or salt or ester thereof and narcotic analgesic or salt thereof present in the present pharmaceutical composition will be determined by, amongst other factors, (a) the number of times per day the composition is to be administered, (b) whether the at least one non-steroidal anti-inflammatory and/or narcotic analgesic phases are a normal or controlled release formulation, and (c) the type of treatment required and stage of treatment reached by the patient.

For most of the therapeutic applications (e.g. treatment of pain and inflammation) envisaged by the present inventors, tablets of the present type will contain an amount of narcotic analgesic and non-steroidal anti-inflammatory carboxylic acid as set out in the Table above. If a salt or ester is employed the dose will be adjusted accordingly to give the required amount of base or acid. Thus, tablets containing ibuprofen and codeine will preferably contain between 50 and 800 mg, especially between 200 and 600 mg, of ibuprofen and between 5 and 60 mg, especially between 7.5 and 30 mg, of codeine.

The amount and/or ratio of self lubricating, compression aids, together with, as required, binders, glidants, anti-adherents, disintegrants, colorants, flavorants, sweeteners, etc. contained in the present pharmaceutical composition is determined by, amongst other factors, (a) the amount of non-steroidal anti-inflammatory carboxylic acid or salt or ester thereof and narcotic analgesic or salt thereof present in the tablet's phases, (b) the requirement of tablet integrity,
(c) the time for tablet disintegration required,
(d) the rate of tablet dissolution required,
(e) the requirement of tablet content uniformity, and
(f) the weight, thickness and size of the tablet.

Given the number of variables involved in the formulation of a pharmaceutical composition according to the present invention, it is difficult to give specific ranges for the concentrations of the above materials. In a preferred embodiment of the present pharmaceutical composition, however, especially wherein the at least one self lubricating compression aid comprises microcrystalline cellulose, the concentration of the compression aid in the at least one non-steroidal anti-inflammatory phase is between 10% and 90%, especially between 15% and 40%, by wt. (of the phase), whilst the concentration of the compression aid in the at least one narcotic analgesic phase is between 50% and 99%, especially between 70% and 95%, by wt. of the phase.

The present pharmaceutical composition may be prepared by direct compression, but is preferably prepared by wet granulation techniques. Thus, in a further aspect of the present invention, there is provided a wet granulation process for the preparation of a pharmaceutical composition according to this invention comprising (a) granulating a narcotic analgesic or an analgesically effective salt thereof with at least one self lubricating, compression aid to form narcotic analgesic granules,
(b) granulating a non-steroidal anti-inflammatory carboxylic acid or an anti-inflammatory salt or ester thereof with at least one self lubricating, compression aid to form non-steroidal anti-inflammatory granules, and
(c) compressing the narcotic analgesic granules and the non-steroidal anti-inflammatory granules to form a multi-phase tablet.

In both steps (a) and (b) of the above process two methods of granulation may be used. In the first method, the drug, the compression aid and a binder are dry mixed. The mixed powders are then granulated by wetting with a solvent. In the second method, the drug and the compression aid are dry mixed and then granulated by wetting with a solution of a binder.

Suitable binders for these methods are hydroxypropylmethyl cellulose or polyvinylpyrrolidone.

The present pharmaceutical composition, together with processes for its preparation, will now be described by way of example only.

COMPARATIVE EXAMPLES

A. Combination of Ibuprofen and Codeine within a Single Layer Tablet with Magnesium Stearate as Lubricant Single layer tablets were prepared from the following ingredients using a wet granulation process,

|  | mg/tablet |
| --- | --- |
| Ibuprofen | 200.00 |
| Codeine Phosphate | 12.50 |
| Microcrystalline Cellulose (Avicel PH 102) | 23.75 |
| Croscarmellose Sodium (Ac-Di-Sol) | 5.00 |

| -continued | |
| --- | --- |
|  | mg/tablet |
| Hydroxypropylmethyl cellulose (6 cps) | 3.75 |
| Magnesium Stearate | 2.45 |

These tablets had poor disintegration times, poor crushing strengths and exhibited sticking problems on compression.

B. Combination of Ibuprofen and Codeine within a Single Layer Tablet

Single layer tablets were prepared from the following ingredients using a wet granulation process.

|  | mg/tablet |
| --- | --- |
| Ibuprofen | 200.0 |
| Codeine Phosphate | 12.5 |
| Microcrystalline cellulose (Avicel PH102, Trade Mark) | 65.4 |
| Sodium Starch Glycollate (Explotab, Trade Mark) | 45.0 |
| Hydroxypropyl methyl cellulose (viscosity, 3 cps) | 7.1 |

When tablets prepared in this manner were compressed to crushing strengths of 9–17 kp, they exhibited sticking and ejection problems. The tablets, when prepared, had unacceptably long disintegration times.

C. Bi-Layer Formulation with Magnesium Stearate Present as a Lubricant

An ibuprofen layer having the following ingredients (in mg) was prepared by a wet granulation process.

| Ibuprofen | 200.00 |
| --- | --- |
| Microcrystalline cellulose (Avicel PH102) | 70.84 |
| Sodium Starch Glycollate (Explotab) | 45.00 |
| Hydroxypropylmethyl cellulose (3 cps) | 8.16 |
| Sodium Lauryl Sulphate | 1.00 |
| Erythrosine Aluminium Lake | 3.28 |

A codeine layer having the following ingredients (in mg) was prepared by a wet granulation process.

| Codeine Phosphate | 12.5 |
| --- | --- |
| Dicalcium Phosphate | 289.5 |
| Hydroxypropylmethyl cellulose (3 cps) | 8.7 |
| Sodium Starch Glycollate | 12.6 |
| Magnesium Stearate | 1.7 |

When the two layers were compressed together the codeine content decreased markedly after short term stability at room and elevated temperatures. Also a brown colour formed, especially at the interface between the two layers.

D. Bi-Layer Formulation with Magnesium Stearate as Lubricant

The ibuprofen layer was prepared as described in Example C. The codeine layer was prepared from the following ingredients (in mg) by a wet granulation process.

| | |
|---|---|
| Codeine Phosphate | 12.5 |
| Microcrystalline cellulose (Avicel PH102) | 267.0 |
| Hydroxypropyl methyl cellulose (3 cps) | 7.0 |
| Sodium Starch Glycollate (intragranular) | 3.0 |
| Sodium Starch Glycollate (extragranular) | 9.0 |
| Magnesium Stearate | 1.5 |

When the codeine layer was compressed it was found that crushing strengths above 6 kp were difficult to achieve even with increasing compression forces.

EXAMPLES ACCORDING TO THE INVENTION

EXAMPLE 1

Ibuprofen Layer

An ibuprofen layer having the following ingredients (in mg) was prepared by a wet granulation process.

| | |
|---|---|
| Ibuprofen | 200.0 |
| Microcrystalline cellulose (Avicel PH102) | 65.0 |
| Sodium Starch Glycollate | 20.0 |
| Hydroxypropylmethyl cellulose (3 cps) | 15.0 |

The ibuprofen, microcrystalline cellulose, sodium starch glycollate and hydroxypropyl methyl cellulose were dry mixed. Water was then added to the dry powder and the mixture was granulated to give pharmaceutical ibuprofen containing granules.

Codeine layer

A codeine layer containing the following ingredients (in mg) was prepared by a wet granulation process.

| | |
|---|---|
| Codeine Phosphate | 12.50 |
| Microcrystalline cellulose (Avicel PH102) | 227.47 |
| Starch 1500 (Trade Mark), Ingragranular | 20.00 |
| Starch 1500, Extragranular | 40.00 |

Codeine Phosphate, microcrystalline cellulose and intragranular Starch 1500 were dry mixed. Water was then added and the mixture was granulated to form pharmaceutical, codeine containing granules. Starch 1500 was then mixed with the granules. Finally the codeine and ibuprofen granules were compressed to give an ibuprofen-codeine bi-layer tablet with a crushing strength of 11–12 kp.

EXAMPLE 2

The procedure of Example 1 was followed except that the ibuprofen layer had the following composition (in mg),

| | |
|---|---|
| Ibuprofen | 200.00 |
| Microcrystalline cellulose (Avicel PH102) | 50.00 |
| Sodium Starch Glycollate | 12.50 |
| Hydroxypropylmethyl cellulose (3 cps) | 12.50 |

EXAMPLE 3

The procedure of Example 1 was followed except that the ibuprofen layer had the following composition (in mg).

| | |
|---|---|
| Ibuprofen | 200.00 |
| Microcrystalline cellulose (Avicel PH102) | 70.84 |
| Sodium Starch Glycollate | 45.00 |
| Hydroxypropylmethyl cellulose (3 cps) | 8.16 |
| Sodium Lauryl Sulphate | 1.00 |
| Erythrosine Aluminium Lake | 3.28 |

The sodium lauryl sulphate and the erythrosine aluminium lake were mixed in the dry powder prior to the addition of water. In this case the resulting tablet was coated using hydroxypropylmethyl cellulose as film former, and PEG400 as plasticiser.

EXAMPLE 4

Ibuprofen Layer

This was prepared as described in Example 3.

Codeine Layer

A codeine layer containing the following ingredients (in mg) was prepared by a wet granulation process.

| | |
|---|---|
| Codeine Phosphate | 12.50 |
| Microcrystalline cellulose (Avicel PH102) | 227.50 |
| Starch 1500 | 40.00 |
| Polyvinylpyrrolidone (Kollidon K30, Trade Mark) | 10.00 |
| Microcrystalline cellulose (Avicel PH101) | 40.00 |

Codeine Phosphate, microcrystalline cellulose (Avicel PH102) and Starch 1500 were dry mixed. An aqueous solution of polyvinylpyrrolidone was then added to the dry powder and the mixture was granulated to give codeine granules. Microcrystalline cellulose (Avicel PH101) was then mixed with the granules. Finally, the codeine and ibuprofen granules were compressed to give an ibuprofen-codeine bilayer tablet with a crushing strength of 11–12 kp.

EXAMPLE 5

The procedure of Example 4 was followed except that the ibuprofen (layer had the following composition (in mg),

| | |
|---|---|
| Ibuprofen | 200.00 |
| Microcrystalline cellulose (Avicel PH102) | 68.59 |
| Sodium Starch Glycollate | 45.00 |
| Hydroxypropylmethyl cellulose (3 cps) | 8.16 |
| Erythrosine Aluminium Lake | 3.25 |

EXAMPLE 6

The procedure of Example 5 was followed except that the amount of Starch 1500 in the codeine layer was reduced to 25.0 mg. In this case the resulting bilayer tablet was coated with hydroxypropylmethyl cellulose as film former, and propylene glycol as plasticiser.

Tablets prepared in accordance with Examples 1 to 6 above exhibited pharmaceutically acceptable properties with regard to stability, disintegration times and dissolution rates.

EXAMPLE 7

Ibuprofen Layer

Ibuprofen (30 gm), microcrystalline cellulose (Avicel pH 102, 5.01 gm), lactose anhydrous (5.01 gm), hydroxyethyl cellulose (0.5 gm), hydroxypropylmethyl cellulose (5cps, 0.95 gm) and trisodium 7-hydroxy-8-(4-sulphonato-1-napthylazo) naphthalene-1,3-di sulphonate (onceau 4R, Trade Mark, 0.43 gm) were dry blended. To the mixture was added sufficient water to produce a granulated mass.

The wet granules were then partially dried in a Fluid Bed dryer at 50° C. The partially dried mass was granulated through a 12 mesh screen and then further dried. The dried granules were passed through a 16 mesh screen. Molten cetostearyl alcohol (1.0 gm) was then added, with mixing, to the granules. Finally, talc (0.4 gm) was blended with the granules.

Codeine Layer

Codeine granules were prepared as described in Example 4 above.

Finally the codeine and the ibuprofen granules were compressed to give an ibuprofen-codeine bilayer tablet containing 300 mg ibuprofen/12.5 mg codeine phosphate and having a controlled release ibuprofen layer and a normal release codeine layer.

Tablets prepared in accordance with Example 7 exhibited pharmaceutically acceptable properties with regard to stability, disintegration times and dissolution rates.

EXAMPLE 8

The procedure of Example 7 was followed except that the codeine layer had the following composition (in mg).

| | |
|---|---|
| Codeine Phosphate | 20.0 |
| Microcrystalline cellulose (Avicel PH 102) | 364.0 |
| Starch 1500 | 40.0 |
| Polyvinylpyrrolidone | 16.0 |
| Microcrystalline cellulose | 64.0 |

Again, tablets prepared in accordance with Example 8 exhibited pharmaceutically acceptable properties with regard to stability, disintegration times and dissolution rates.

EXAMPLE 9

The procedure of Example 8 was followed. The tablets were then film coated with hydroxypropylmethyl cellulose as film former and propylene glycol as plasticiser.

EXAMPLE 10

The procedure of Example 4 was followed except that the codeine layer had the following composition (in mg).

| | |
|---|---|
| Codeine Phosphate | 12.5 |
| Microcrystalline cellulose (Avicel PH 102) | 227.5 |
| Starch 1500 | 60.0 |

The tablets were film coated with hydroxypropylmethyl cellulose as film former and polyethylene glycol as plasticiser.

EXAMPLE 11

The procedure of Example 4 was followed except that dihydrocodeine tartrate replaced codeine phosphate and the dihydrocodeine layer had the following composition (in mg).

| | |
|---|---|
| Dihydrocodeine tartrate | 30.0 |
| Microcrystalline cellulose (Avicel PH 102) | 200.0 |
| Starch 1500 | 40.0 |
| Polyvinylpyrrolidone (PVP-K30) | 10.0 |
| Microcrystalline cellulose (Avicel PH 101) | 30.0 |

EXAMPLE 12

The procedure of Example 4 was followed except that naproxen replaced ibuprofen and the naproxen layer had the following composition (in mg).

| | |
|---|---|
| Naproxen | 500.0 |
| Microcrystalline cellulose (Avicel PH 102) | 150.0 |
| Starch 1500 | 45.0 |
| Sodium Starch Glycollate (Explotab) | 100.0 |
| Hydroxypropylmethyl cellulose | 20.0 |

EXAMPLE 13

The procedure of Example 4 was followed except that flurbiprofen replaced ibuprofen and the flurbiprofen layer had the following composition (in mg).

| | |
|---|---|
| Flurbiprofen | 100.0 |
| Microcrystalline cellulose (Avicel PH 102) | 35.0 |
| Sodium Starch Glycollate | 20.0 |
| Hydroxypropylmethyl cellulose | 5.0 |
| Erythrosine Aluminium Lake | 1.5 |

What I claim is:

1. A pharmaceutical composition in the form of a multiphase tablet comprising at least one narcotic analgesic phase containing a therapeutically effective quantity of a narcotic analgesic or an analgesically effective salt thereof and at least one non-steroidal anti-inflammatory phase containing a therapeutically effective quantity of a non-steroidal anti-inflammatory carboxylic acid or an anti-inflammatory salt or ester thereof wherein the at least one narcotic analgesic phase is free from a non-steroidal anti-inflammatory carboxylic acid or salt or ester thereof, stearic acid and a stearate salt, and the at least one non-steroidal anti-inflammatory phase is free from a narcotic analgesic or salt thereof, stearic acid and a stearate salt, and further wherein both the at least one narcotic analgesic phase and the at least one non-steroidal anti-inflammatory phase contain at least one self-lubricating, compression aid.

2. A composition according to claim 1 wherein the narcotic analgesic comprises a morphinan-6-ol or a morphinan-6-one derivative, selected from morphine, ethylmorphine, hydromorphone, hydrocodone, dihydrocodeine and codeine.

3. A composition according to claim 1 wherein the analgesically effective salt of the narcotic analgesic comprises codeine phosphate.

4. A composition according to claim 1 wherein the non-steroidal anti-inflammatory carboxylic acid comprises at least one of naproxen, a benzeneacetic acid, selected from alclofenac, diclofenac and fenclofenac, and a 2-phenylpropionic acid, selected from fenoprofen, flurbiprofen, indoprofen, ketoprofen and ibuprofen.

5. A composition according to claim 4 wherein the non-steroidal anti-inflammatory carboxylic acid comprises ibuprofen.

6. A composition according to claim 1 wherein the at least one self lubricating, compression aid comprises at least one self lubricating, direct compression aid, selected from microcrystalline cellulose and a free flowing, directly compressible starch.

7. A composition according to claim 1 wherein the concentration of the compression aid in the at least one non-steroidal anti-inflammatory phase is between 10% and 90% (by wt).

8. A composition according to claim 7 wherein the concentration is between 15% and 40% (by wt).

9. A composition according to claim 1 wherein the concentration of the compression aid in the at least one narcotic analgesic phase is between 50% and 99% (by wt).

10. A composition according to claim 9 wherein the concentration is between 70% and 95% (by wt).

11. A composition according to claim 1 in the form of a layered tablet.

12. A composition according to claim 11 in the form of a bilayered tablet.

13. A wet granulation process for the preparation of a pharmaceutical composition according to claim 1 comprising
  (a) granulating a narcotic analgesic or an analgesically effective salt thereof with at least one self-lubricating, compression aid to form narcotic analgesic granules,
  (b) granulating a non-steroidal anti-inflammatory carboxylic acid or an anti-inflammatory salt or ester thereof with at least one self lubricating, compression aid to form non-steroidal anti-inflammatory granules, and
  (c) compressing the narcotic analgesic granules and the non-steroidal anti-inflammatory granules to form a multiphase tablet.

* * * * *